US011241160B2

United States Patent
Shinzato et al.

(10) Patent No.: US 11,241,160 B2
(45) Date of Patent: Feb. 8, 2022

(54) BLOOD PRESSURE MEASURING DEVICE (71) Applicant: NIPRO CORPORATION, Osaka (JP)

(72) Inventors: Toru Shinzato, Aichi (JP); Masamiki Miwa, Aichi (JP); Mitsutaka Ueda, Osaka (JP); Makoto Mitsuhashi, Osaka (JP); Hironori Numoto, Osaka (JP)

(73) Assignee: NIPRO CORPORATION, Osaka (JP)

( * ) Notice: Subject to any disclaimer, the term of this patent is extended or adjusted under 35 U.S.C. 154(b) by 140 days.

(21) Appl. No.: 15/564,527

(22) PCT Filed: Mar. 23, 2016

(86) PCT No.: PCT/JP2016/001697
§ 371 (c)(1),
(2) Date: Oct. 5, 2017

(87) PCT Pub. No.: WO2016/163093
PCT Pub. Date: Oct. 13, 2016

(65) Prior Publication Data
US 2018/0070838 A1    Mar. 15, 2018

(30) Foreign Application Priority Data

Apr. 8, 2015  (JP) .............................. JP2015-079527

(51) Int. Cl.
*A61B 5/022* (2006.01)
*A61B 5/02* (2006.01)
*A61B 5/00* (2006.01)

(52) U.S. Cl.
CPC .......... *A61B 5/02241* (2013.01); *A61B 5/022* (2013.01); *A61B 5/02007* (2013.01);
(Continued)

(58) Field of Classification Search
CPC .............. A61B 5/02241; A61B 5/6831; A61B 5/02007; A61B 5/7278; A61B 5/4848;
(Continued)

(56) References Cited

U.S. PATENT DOCUMENTS 3,124,132 A    3/1964  Sullivan et al.
4,597,393 A *  7/1986  Yamakoshi ........ A61B 5/02255
                                                 600/479
(Continued)

FOREIGN PATENT DOCUMENTS

CN    103889318 A    6/2014
JP    09-294730 A    11/1997
(Continued)

OTHER PUBLICATIONS

Extended European Search Report dated Feb. 27, 2018 for corresponding European Application No. 16776271.5.
(Continued)

*Primary Examiner* — Allen Porter
*Assistant Examiner* — Abid A Mustansir
(74) *Attorney, Agent, or Firm* — Renner, Otto, Boisselle & Sklar, LLP (57) ABSTRACT

Disclosed herein is a blood pressure measuring device including: a pressure measuring tool 110; a fastening member 120 configured to fasten the pressure measuring tool 110 in rest position onto a skin region covering an anastomotic region of a shunt blood vessel 201; and a control circuit 130 configured to receive an input signal from the pressure measuring tool 110 and to process the input signal to calculate a pressure inside the anastomotic region of the shunt blood vessel 201.

8 Claims, 4 Drawing Sheets

(52) U.S. Cl.
CPC .......... *A61B 5/4848* (2013.01); *A61B 5/6831* (2013.01); *A61B 5/7278* (2013.01); *A61B 2562/0261* (2013.01)

(58) Field of Classification Search
CPC ............ A61B 5/022; A61B 2562/0261; A61B 5/6824; A61B 5/02
See application file for complete search history.

(56) References Cited

U.S. PATENT DOCUMENTS

| | | | | |
|---|---|---|---|---|
| 4,993,422 | A * | 2/1991 | Hon | A61B 5/02241 600/485 |
| 5,351,694 | A | 10/1994 | Davis et al. | |
| 5,848,970 | A | 12/1998 | Voss et al. | |
| 6,348,038 | B1 * | 2/2002 | Band | A61B 5/029 600/485 |
| 2002/0095092 | A1 * | 7/2002 | Kondo | A61B 5/02116 600/503 |
| 2004/0203414 | A1 * | 10/2004 | Satou | H04M 1/03 455/66.1 |
| 2005/0065442 | A1 * | 3/2005 | Hashimoto | A61B 5/021 600/501 |
| 2009/0138636 | A1 * | 5/2009 | Burton | A63B 24/00 710/63 |
| 2011/0208070 | A1 | 8/2011 | Sawanoi et al. | |
| 2012/0277597 | A1 | 11/2012 | Eshbaugh et al. | |
| 2013/0085357 | A1 | 4/2013 | Huber et al. | |
| 2017/0011210 | A1 * | 1/2017 | Cheong | A61B 5/0022 |

FOREIGN PATENT DOCUMENTS

| | | |
|---|---|---|
| JP | 11-113862 A | 4/1999 |
| JP | 2001-087231 A | 4/2001 |
| JP | 2002-224064 A | 8/2002 |
| JP | 2008-012230 A | 1/2008 |
| JP | 2010-110375 A | 5/2010 |
| JP | 2010-179054 A | 8/2010 |
| JP | 2011-098090 A | 5/2011 |
| JP | 2012-152372 A | 8/2012 |
| JP | 2013-078579 A | 5/2013 |
| WO | WO 2004/069049 | 8/2004 |

OTHER PUBLICATIONS

International Search Report for corresponding International Application No. PCT/JP2016/001697 dated May 31, 2016.
Thirty (30) Days Have not Elapsed Since the Receipt of the Office Action in Which the Above References were First Cited.

* cited by examiner

BLOOD PRESSURE MEASURING DEVICE

TECHNICAL FIELD

The present disclosure relates to a blood pressure measuring device.

BACKGROUND ART

When a hemodialysis is performed, in order to allow a sufficient amount of blood to circulate extracorporeally, the artery in a deep region of a patient's arm is connected (anastomosed) by surgery to the vein in his or her subcutaneous tissue, thus providing a shunt blood vessel such that blood directly flows from the artery into the vein without passing through capillaries.

Meanwhile, during the hemodialysis, blood pressure sometimes decreases. That is why during the hemodialysis, it is recommended that blood pressure be measured frequently. Currently, blood pressure is generally measured by the following method: First, one of the arms with no shunt blood vessel is wrapped with a cuff, which is then inflated to squeeze the artery completely, thus temporarily stopping arterial blood flow. Thereafter, the cuff pressure is gradually lowered to measure a pressure at which blood starts flowing again through the artery. The reperfusion of the arterial blood flow is detected by sensing either the noise (Korotkov's sound) caused by the arterial blood flow or the vibration of the skin over the artery. According to this blood pressure measuring method, the blood flow is once stopped with the artery squeezed with the cuff, and therefore, the blood pressure of a patient cannot be measured on his or her arm with a shunt blood vessel provided to allow a sufficient amount of blood to circulate extracorporeally. This forces the patient to undergo a hemodialysis with one of his or her arm with the shunt blood vessel, provided to allow a sufficient amount of blood to circulate extracorporeally, and the other arm of his or hers, on which his or her blood pressure is being measured, both put in rest position, thus causing a great deal of discomfort to him or her. In addition, this method does not allow his or her blood pressure to be measured continuously.

Thus, a continuous blood pressure measuring method has been proposed as an alternative method for measuring the blood pressure without temporarily stopping the blood flow (see, for example, Patent Document 1). According to this alternative method, a pressure sensor is put on the patient's arm skin over the artery. Next, a flexible bag, having an inflatable and shrinkable internal chamber and made of fabric, rubber, a synthetic resin, or any other suitable material, is further placed on the pressure sensor. Then, the flexible bag is fastened with a band made of fabric, rubber, a synthetic resin, or any other suitable material, and inflated to produce a pressure that is not so high as to completely squeeze the artery. In this state, the arterial pressure (blood pressure) applied to the pressure sensor is measured continuously.

CITATION LIST

Patent Documents

PATENT DOCUMENT 1: WO 2004/069049

Non-Patent Documents

NON-PATENT DOCUMENT 1: McGee at al., "Critical Care," $V_0$l. 11, No. 5

NON-PATENT DOCUMENT 2: Genji Yamanaka, "Intensive Care for Seriously Injured," $V_0$l. 13, No. 1, p. 13

NON-PATENT DOCUMENT 3: McGee W T, Horswell J L, and Calderon J: "Validation of a Continuous Cardiac Output Measurement Using Arterial Pressure Waveforms," Crit Care, 2005, $V_0$l. 9, pp. 24-25

SUMMARY

Technical Problem

However, attempting to measure a patient's blood pressure by such a method on his or her arm provided with the shunt blood vessel will make the pressure sensor, fastened with the band and the flexible bag, waver as his or her blood pressure, of which the highest value is defined by a systolic blood pressure and the lowest value is defined by a diastolic blood pressure, varies in a period of approximately one second. Thus, the pressure variation detected by the pressure sensor attenuates too much to measure the blood pressure accurately.

Meanwhile, the blood pressure is determined by a cardiac output representing the amount of blood pumped out of the heart and by a peripheral vascular resistance produced by a peripheral contraction of the systemic blood vessel. That is why if the blood pressure decreases during the hemodialysis, either the cardiac output or the peripheral vascular resistance decreases (see, for example, Non-Patent Document 1). In other words, measuring the cardiac output and the peripheral vascular resistance during the hemodialysis would allow a decrease in blood pressure during the hemodialysis to be predicted. Actually, however, the peripheral vascular resistance is calculated by dividing the blood pressure by the cardiac output. Thus, once the cardiac output has been measured, a decrease in blood pressure during the hemodialysis is predictable.

Nevertheless, to measure the cardiac output, a catheter needs to be inserted deep into the pulmonary vein through the aorta (see, for example, Non-Patent Document 2), which makes it virtually impossible to continuously measure the cardiac output, as well as the blood pressure, during the hemodialysis.

According to another method for measuring the cardiac output, a catheter is inserted into the artery to analyze an arterial waveform thus measured (see, for example, Non-Patent Document 3). This method also requires directly inserting a catheter into the artery, which makes it virtually impossible, either, to continuously measure the cardiac output, as well as the blood pressure, during the hemodialysis.

Solution to the Problem

A blood pressure measuring device according to an aspect of the present disclosure includes: a pressure measuring tool; a fastening member configured to fasten the pressure measuring tool in rest position onto a skin region covering an anastomotic region of a shunt blood vessel; and a control circuit configured to receive an input signal from the pressure measuring tool and to process the input signal to calculate a pressure inside the anastomotic region of the shunt blood vessel. This configuration substantially eliminates the waver of the pressure measuring tool with the anastomotic region's pulsation, thus allowing the pressure inside the anastomotic region to be measured accurately and continuously. In addition, this configuration also allows for obtaining an arterial waveform because the pressure inside the anastomotic region is virtually equal to the arterial pressure.

In one embodiment of the blood pressure measuring device according to the present disclosure, the fastening member may keep a distance constant between the pressure measuring tool and a surface of the skin region opposite from the pressure measuring tool. Normally, the anastomotic region of a shunt blood vessel is present stably right over the radius and ulna of a patient's forearm. Thus, supposing the radius and ulna are located under the anastomotic region, the lower wall of the anastomotic region does not waver as the anastomotic region pulsates, while the upper wall of the anastomotic region vertically wavers. Thus, keeping the distance constant between the pressure measuring tool and the surface of the skin region opposite from the pressure measuring tool allows the pressure inside the anastomotic region to be measured accurately and continuously with the pressure measuring tool fastened in rest position onto the skin region covering the anastomotic region of the shunt blood vessel.

In another embodiment of the blood pressure measuring device according to the present disclosure, the fastening member may be an inflexible band to wrap around an arm at a site where there is the anastomotic region of the shunt blood vessel.

In still another embodiment of the blood pressure measuring device according to the present disclosure, a portion of the inflexible band to contact with the surface of the skin region opposite from the pressure measuring tool may have a larger area than another portion of the inflexible band to contact with the pressure measuring tool. This configuration decreases the pressure applied from the portion of the inflexible band to contact with the surface of the skin region opposite from the pressure measuring tool to the arm. Thus, even wrapping the arm with the inflexible band does not obstruct the blood flow through the arm's vein.

In yet another embodiment of the blood pressure measuring device according to the present disclosure, the pressure measuring tool may have a flat plate shape. The pressure measuring tool in such a flat plate shape is unlikely to do damage to the anastomotic region.

In yet another embodiment of the blood pressure measuring device according to the present disclosure, the pressure measuring tool may have a curved surface. Implementing a pressure measuring tool with a curved surface, of which the area is large enough to fully cover the anastomotic region raised from under the skin, allows for measuring the pressure inside the anastomotic region while protecting the anastomotic region.

In yet another embodiment of the blood pressure measuring device according to the present disclosure, the pressure measuring tool may include a strain sensor.

In yet another embodiment of the blood pressure measuring device according to the present disclosure, the control circuit may continuously process the input signal received from the pressure measuring tool to calculate a periodic change in pressure inside the anastomotic region as a continuous waveform.

In yet another embodiment of the blood pressure measuring device according to the present disclosure, the control circuit may respectively calculate a highest pressure and a lowest pressure inside the anastomotic region based on a local maximum value and a local minimum value of the continuous waveform.

In yet another embodiment of the blood pressure measuring device according to the present disclosure, the control circuit may calculate a cardiac output based on the continuous waveform. A blood pressure measuring device according to the present disclosure can obtain at least as accurate an arterial waveform as the one measured with a catheter inserted into the artery, and therefore, can calculate a cardiac output by analyzing the arterial waveform.

Advantageous of the Invention

A blood pressure measuring device according to the present disclosure can not only measure the blood pressure and obtain an arterial waveform both accurately and continuously but also estimate a variation in cardiac output as well.

DESCRIPTION OF EMBODIMENTS

Figure 1:
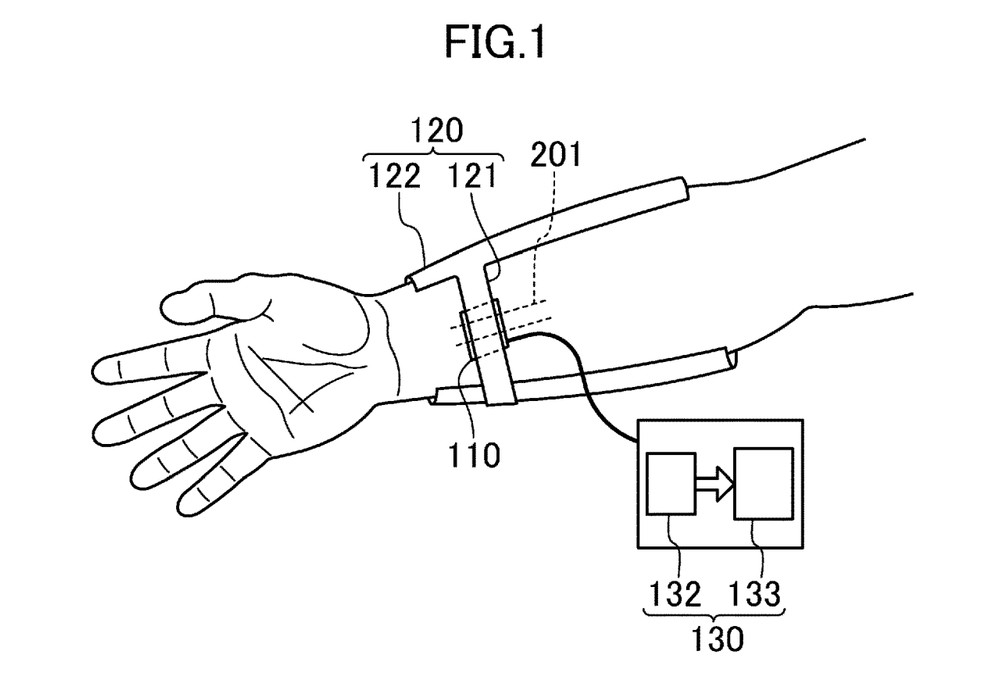
FIG. 1 Illustrates an exemplary blood pressure measuring device.
Figure 2:
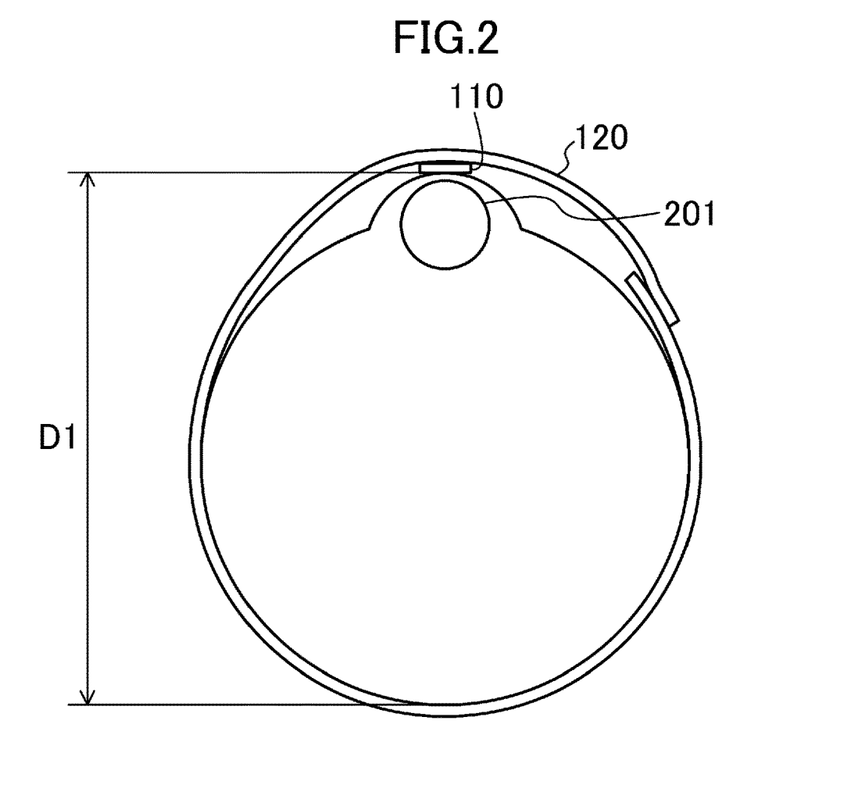
FIG. 2 A cross-sectional view illustrating how a sensor may be fastened in an exemplary embodiment.

FIG. 1 illustrates, by way of example, a situation where a shunt blood vessel is formed in a patient's forearm. A blood pressure measuring device according to this embodiment includes: a strain sensor 110 serving as an exemplary pressure measuring tool; and a band 120 serving as an exemplary fastening member. As shown in FIG. 1, the strain sensor 110 as an exemplary pressure measuring tool is fastened, with the band 120 as an exemplary fastening member, onto the patient's skin region over an anastomotic region of a shunt blood vessel 201. As used herein, the "shunt blood vessel" refers to the vein directly connected to the artery to extract blood from the patient's body. The "anastomotic region" refers herein to a portion of the shunt blood vessel in the vicinity of another portion thereof connected to the artery. The intravascular pressure inside the anastomotic region (hereinafter referred to as an "anastomotic region pressure") is equal to the blood pressure. Thus, measuring the anastomotic region pressure allows for measuring the blood pressure. At the anastomotic region, the blood vessel is approximately one-tenth as thick as the artery. Also, anatomically speaking, the anastomotic region is located right under the skin. Thus, as shown in FIG. 2, the anastomotic region is raised due to the intravascular pressure and protrudes with respect to the other area of the skin. For this reason, the intravascular pressure can be extracorporeally measured more easily at the anastomotic region than at the artery.

Meanwhile, the anastomotic region is susceptible to an external force far more easily than the artery is. That is why if a sensor for measuring the intravascular pressure had such a shape as easily hurting the skin over the anastomotic region and the vascular wall of the anastomotic region, then the anastomotic region could be hurt so much as to make the patient bleed profusely, and in a worst-case scenario, even bring him or her to death. Therefore, the strain sensor suitably either has a flat plate shape or is curved along the anastomotic region.

In FIG. 1, the fastening member is implemented as a band 120 made of an inflexible material. Wrapping the arm having the shunt blood vessel 201 with the band 120 at the anastomotic region allows the strain sensor 110 to be fastened onto the skin over the anastomotic region such that the anastomotic region of the shunt blood vessel 201 is not blocked but still deformed.

Normally, the anastomotic region of the shunt blood vessel is present stably right over the radius and ulna of a patient's forearm. Thus, supposing the radius and ulna are located under the anastomotic region, the lower wall of the anastomotic region does not waver as the pressure inside the anastomotic region varies, while the upper wall of the anastomotic region vertically wavers. Thus, the distance D1 between the surface of the skin opposite from the anastomotic region and the surface of the skin over the shunt blood vessel (i.e., the bottom of the strain sensor 110) does not vary. In such a state, the periodically varying pressure inside the anastomotic region of the shunt blood vessel is directly applied in real time to the strain sensor 110. This allows the pressure waveform inside the anastomotic region, i.e., arterial waveform, to be measured accurately.

Optionally, the band 120 may have its length adjusted such that the strain sensor 110 can be fastened onto the skin over the anastomotic region with the anastomotic region of the shunt blood vessel 210 not blocked but still deformed.

Figure 3:
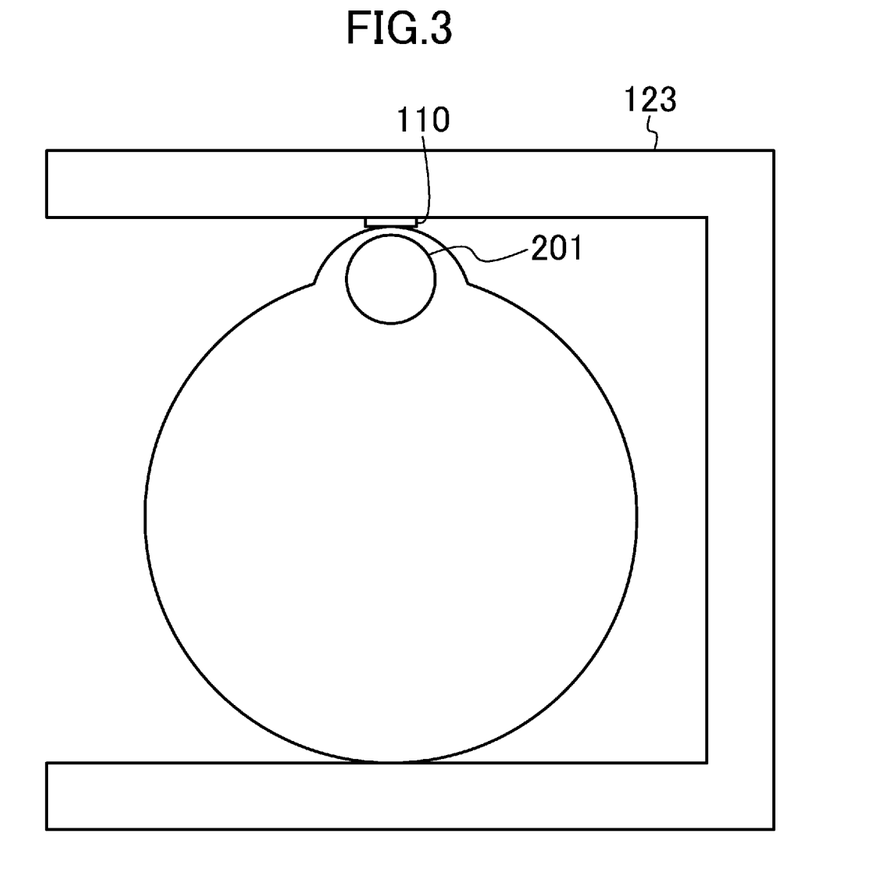
FIG. 3 A cross-sectional view illustrating an exemplary sensor holder.

In FIG. 1, the band 120 includes a body portion 121 of a narrower width to contact with the strain sensor 110 and a broader portion 122 of a broader width than the body portion. The broader portion 122 contacts with a portion of the arm opposite from the anastomotic region. Providing the broader portion 122 allows the pressure applied from the band 120 to that portion of the arm opposite from the anastomotic region to be distributed broadly. That is to say, this weakens the pressure applied from the band 120 to that portion of the arm opposite from the portion to which the strain sensor 110 is fastened. This reduces the possibility of causing hemostasis upstream of the region provided with the band 120, thus allowing the patient to wear this blood pressure measuring device more comfortably. Note that the fastening member just needs to fasten the strain sensor 110 such that the anastomotic region of the shunt blood vessel 201 is not blocked but still deformed and that the distance between the surface of the skin opposite from the anastomotic region of the arm and the strain sensor 110 does not vary. That is why the fastening member does not have to be the band but may also be a holder 123 with a U-cross section such as the one shown in FIG. 3, for example. The holder 123 may be made of a resin, a metal, or any other suitable material.

Any type of strain sensor may be used as the strain sensor 110 serving as the pressure measuring tool, as long as the sensor can detect the periodic pressure variation in the anastomotic region of the shunt blood vessel 201. Nevertheless, the strain sensor 110 suitably has as high sensitivity as possible and as low power consumption as possible. For example, a strain sensor, having a gauge factor of at least 2, suitably equal to or greater than 5, more suitably equal to or greater than 10, and even more suitably equal to or greater than 20, may be used. Specifically, a metallic resistance strain sensor, a semiconductor strain sensor, a magnetostrictive effect strain sensor, or any other suitable type of strain sensor may be used, for example. Among other things, it is recommended to use a semiconductor strain sensor that uses a semiconductor piezoelectric resistance, because that type of sensor has high sensitivity and low power consumption. Furthermore, the strain sensor 110 suitably has a flat plate shape, because the strain sensor of that type can be easily fastened over the anastomotic region of the shunt blood vessel 201 and carries a low risk of hurting the anastomotic region of the shunt blood vessel. A small-sized strain sensor of approximately 5 mm to 2 cm square is particularly suitable, because such a small strain sensor can be easily fastened over the anastomotic region of the shunt blood vessel 201.

Figure 4:
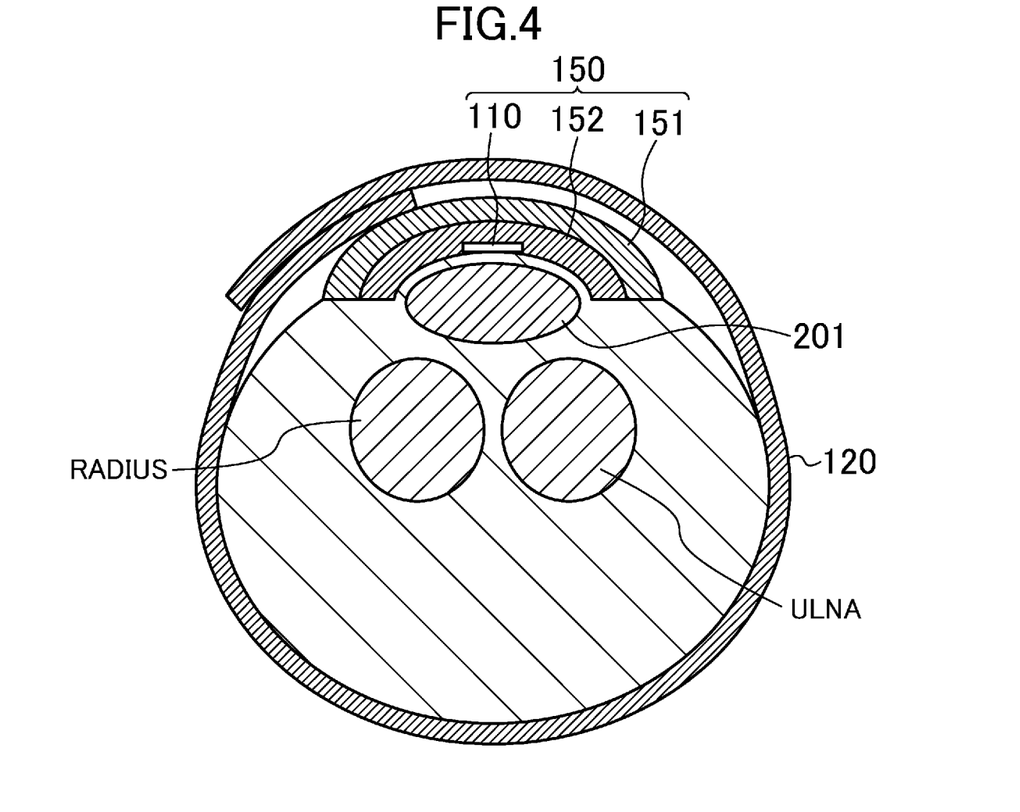
FIG. 4 A cross-sectional view illustrating how a sensor may be fastened in another exemplary embodiment.

The pressure measuring tool may be a combination of the strain sensor 110 and any other type of member. In that case, the pressure measuring tool may have the shape of a dish with a curved surface that can cover the anastomotic region raised from under the skin. Covering the anastomotic region of the shunt blood vessel 201 with such a dish-shaped cover having a curved surface during the hemodialysis would significantly reduce the risk of the anastomotic region being hurt due to an external force. As shown in FIG. 4, the dish-shaped pressure measuring tool 150 having a curved surface has its outer surface implemented as a plastic cover 151 and its inner surface implemented as a gelled liquid bag 152, to which the strain sensor 110 is adhered. The gelled liquid bag 152 is a flexible bag having a constant volume, and is enclosed in a space formed by a plastic cover. Thus, the gelled liquid bag 152 turns into a dish shape having a curved surface with a virtually constant width, covering the anastomotic region of the shunt blood vessel 201. Therefore, the distance D1 between the strain sensor 110 adhered to the gelled liquid bag 152 that has turned into a dish shape having a curved surface with a virtually constant width and the arm's skin region opposite from the strain sensor 110 is constant. As long as the anastomotic region is deformed+ with the gelled liquid bag 152, the pressure is directly applied from the anastomotic region to the strain sensor 110. The strain sensor 110 itself has a plate shape, and therefore, does not hurt the anastomotic region.

The anastomotic region pressure measuring device according to this embodiment includes a control circuit 130 which drives the strain sensor 110, receives a signal from the strain sensor 110, and processes the signal, thereby calculating the pressure inside the anastomotic region. The control circuit 130 includes a driver 132 for driving the strain sensor 110 and a processor 133 for processing the output signal of the strain sensor 110.

An appropriate circuit may be selected as the driver 132 depending on the type of the strain sensor 110 to use. If the strain sensor selected produces a resistance variation, a Wheatstone bridge circuit may be used, for example.

The processor 133 may include a converter for converting the signal received from the strain sensor 110 into digital data, and an arithmetic circuit for calculating the pressure inside the anastomotic region by performing arithmetic processing on the digital data. Optionally, the processor 133 may further include a memory circuit for storing signal data and processed data and a display device for displaying the results. When provided, the display device may display either only the value of the pressure inside the anastomotic region or the pressure value and an output signal waveform of the strain sensor 110 in combination. If necessary, not only the pressure inside the anastomotic region but also other types of data such the patient's body temperature may be displayed as well. Alternatively, the processor 133 may have no display and may be configured to transmit data to a central processing unit with a built-in computer and other devices, perform batch processing on not only the data but also other kinds of information collectively, and display the results.

Figure 5:
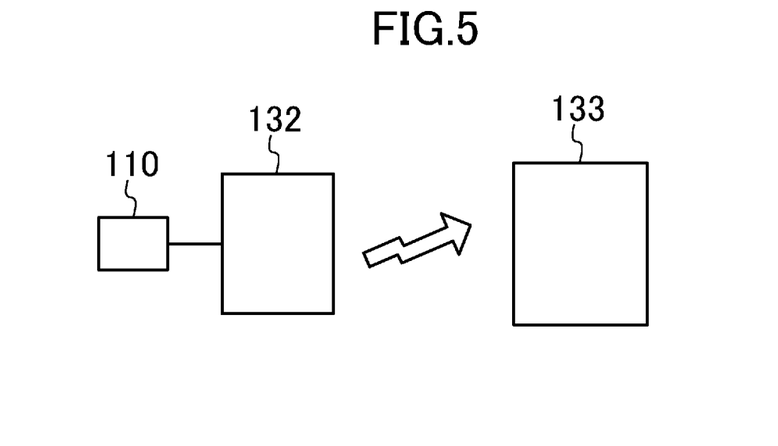
FIG. 5 Illustrates a variation of the blood pressure measuring device.

Although the driver 132 and the processor 133 are integrated together in the control circuit 130 in the example illustrated in FIG. 1, the driver 132 and the processor 133 may be separated from each other as shown in FIG. 5. In that case, performing wireless communication between the driver 132 and the processor 133 would facilitate providing the processor 133 at a remote location distant from the patient. Even so, just placing a sensor and minimum required driver and communications circuit on the patient's body surface allows his or her blood pressure to be monitored continuously. This significantly alleviates the burden on the patient who is having his or her blood pressure measured. Optionally, the driver 132 and the processor 133 may be hardwired with each other.

Figure 6:
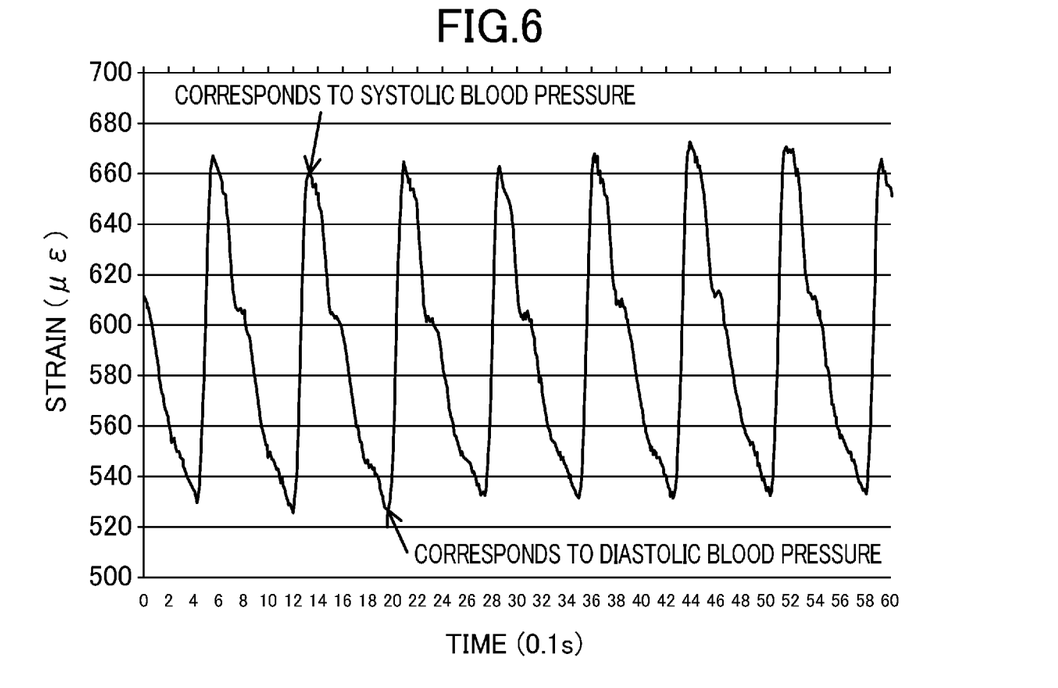
FIG. 6 Shows an exemplary output of a strain sensor.

FIG. 6 shows an exemplary output waveform of the strain sensor 110. In FIG. 6, the ordinate represents the strain (in µε) and the abscissa represents the time (in 0.1 s). The anastomotic region of the shunt blood vessel, which is a region where the vein is anastomosed to the artery, dilates and contracts as the heart contracts and dilates. The anastomotic region of the shunt blood vessel is located near the patient's body surface and has a thin wall. Thus, the pulse waves coming from the anastomotic region are directly reflected on the skin surface to produce a minimal strain on the skin surface. Thus, putting a stain sensor on the skin over the anastomotic region to detect the strain on the skin surface allows for obtaining a signal representing the contraction of the anastomotic region of the shunt blood vessel. The output signal of the strain sensor 110 arranged over the anastomotic region of the shunt blood vessel a shown in FIG. 2 basically draws an amplitude waveform having local maximum and local minimum values. This waveform may be regarded as an arterial pressure waveform. The local maximum value represents the strain produced in the anastomotic region of the shunt blood vessel due to the contraction of the heart, while the local minimum value represents the strain produced in the anastomotic region of the shunt blood vessel due to the dilatation of the heart. Thus, the local maximum value of the arterial pressure waveform is correlated to the highest pressure inside the anastomotic region of the shunt blood vessel (which is equal to a systolic blood pressure), while the local minimum value thereof is correlated to the lowest pressure inside the anastomotic region of the shunt blood vessel (which is equal to a diastolic blood pressure).

Placing, before using the blood pressure measuring device, the strain sensor of the device on the flat surface of a stage, and then putting a predetermined weight (e.g., a weight of 136 g having a bottom area of 1 cm$^2$) on the strain sensor (which applies a pressure of 100 mmHg to the strain sensor) allows the strain sensor to be calibrated. In this manner, the conversion factor can be calculated based on the strain produced by putting the weight on the strain sensor and the strain under the atmospheric pressure.

As can be seen from the foregoing description, the blood pressure measuring device according to this embodiment can obtain the arterial pressure waveform continuously. Thus, even though it is a noninvasive device, the shunt blood pressure measuring device according to this embodiment allows the blood pressure to be monitored continuously.

The "blood pressure" generally measured is the pressure inside the artery. However, to exhibit its property of being able to have a high intravascular pressure, the artery is located relatively deep under the body surface so as not to be easily affected by an externally applied physical force. That is why to obtain an arterial pulse wave, the artery is generally strongly compressed or even invaded.

On the other hand, the anastomotic region of the shunt blood vessel is located right under the skin and has a wall which is just one-tenth as thick as the artery and which is significantly dilated. Thus, putting a sensor over the anastomotic region of the shunt blood vessel and fastening the sensor so that its position does not change even as the anastomotic region of the shunt blood vessel dilates or contracts will allow for obtaining a waveform corresponding to the arterial pulse wave and calculating, based on the waveform, the pressure inside the anastomotic region corresponding to the blood pressure. However, the structure of the anastomotic region of the shunt blood vessel would make the anastomotic region easily affected by an external physical force. Once the anastomotic region has been affected, there is a significantly increased risk of its rupture. In that case, it is not beneficial to apply varying pressures to the anastomotic region or to press a sensor with a protruding portion against the anastomotic region. Taking these disadvantages into account, according to this embodiment, the pressure inside the anastomotic region is measured with a flat plate sensor with no protruding portion. In addition, according to this embodiment, covering the anastomotic region with a curved pressure measuring site allows for measuring the pressure inside the anastomotic region while protecting the anastomotic region.

For example, in the case of a forearm, the shunt blood vessel may be formed of the vein located between the skin surface and the radius and ulna. These two bones play the role of a hard bed to put the anastomotic region of the shunt blood vessel on. Thus, even if the raised anastomotic region is pressed downward, the anastomotic region of the shunt blood vessel is supported by those two bones and does not move downward. Fastening the strain sensor on the skin over the anastomotic region such that the distance between the skin surface opposite from the arm's anastomotic region and the strain sensor does not vary with the anastomotic region raised just like an aneurysm not blocked, but still deformed, with the compression via the strain sensor will prevent the anastomotic region from moving downward. As a result, the pressure inside the anastomotic region (i.e., the blood pressure) is directly applied to the strain sensor. Compressing the raised anastomotic region with the use of a flexible band or cuff would allow the strain sensor to move up and down as the pressure inside the anastomotic region of the shunt blood vessel varies, thus making the blood pressure waveform detected gentler than that of an actual wave.

Using the blood pressure measuring device according to this embodiment allows for continuously monitoring not only the blood pressure but also the cardiac output as well.

Figure 7:
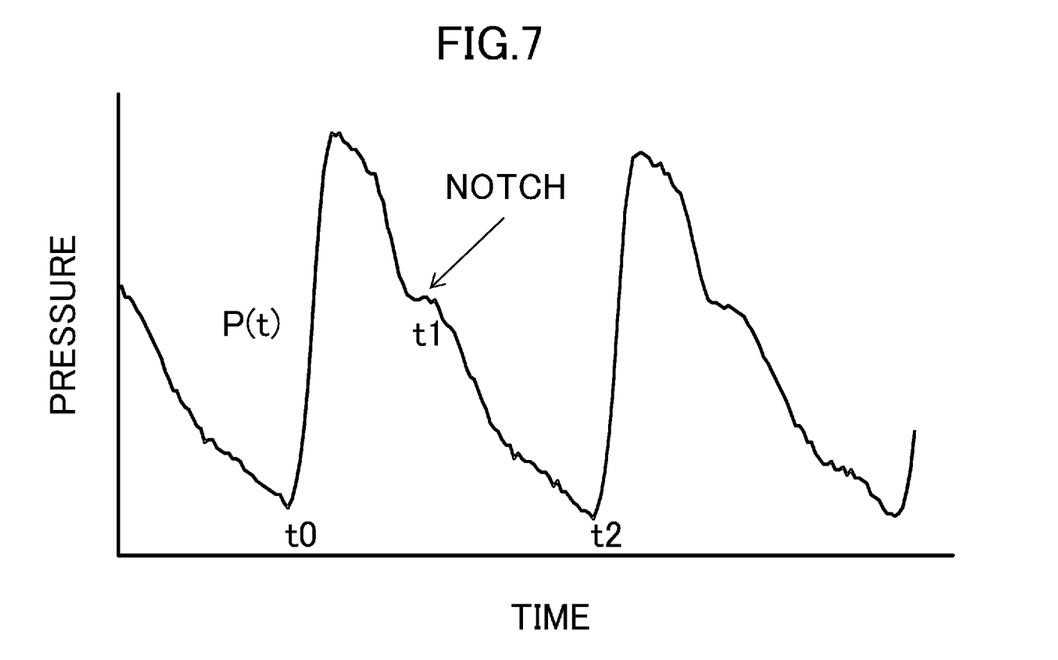
FIG. 7 Shows how to calculate a cardiac output.

Next, it will be described how to obtain the cardiac output by analyzing the pressure waveform (which is virtually equal to the arterial waveform) of the pressure measured inside the anastomotic region by the blood pressure measuring device according to the present disclosure. First, the systolic phase start point of the pressure waveform representing the pressure inside the anastomotic region is supposed to be time t=0. If, on the pressure waveform representing the pressure inside the anastomotic region, the amount of the arterial blood flow at the time t is V(t), the cardiac output (stroke volume) is SV(t), and the amount of blood flowing out into the capillaries is Q(t), then in the systolic phase (i.e., the phase in which the aortic valve is opened and which precedes the notch on the pressure waveform shown in FIG. 7), the following Equation (1) is satisfied:

$$\frac{dV(t)}{dt} = SV(t) - Q(t) \tag{1}$$

On the other hand, supposing the amount Q(t) of blood flowing out into the capillaries is proportional to the blood pressure P(t) and inversely proportional to the total peripheral vascular resistance R, the following Equation (2) is satisfied:

$$Q(t) = \frac{P(t)}{R} \tag{2}$$

The following Equation (3) is derived by substituting Equation (2) for Equation (1):

$$\frac{dV(t)}{dt} = SV(t) - \frac{P(t)}{R} \tag{3}$$

Furthermore, supposing the amount V(t) of the arterial blood flow is proportional to the blood pressure P(t), the following Equation (4) is obtained:

$$V(t) = \alpha \times P(t) + V_{const} \tag{4}$$

The following Equation (5) is derived by differentiating both sides of Equation (4) with t.

$$\frac{dV(t)}{dt} = \alpha \frac{dP(t)}{dt} \tag{5}$$

The following Equation (6) is derived by substituting Equation (5) for Equation (3):

$$\alpha \frac{dP(t)}{dt} = SV(t) - \frac{P(t)}{R} \tag{6}$$

Equation (6) may be rewritten into the following Equation (7):

$$SV(t) = \alpha \frac{dP(t)}{dt} + \frac{P(t)}{R} \tag{7}$$

Therefore, the stroke volume SV may be given by the following Equation (8), where t1 represents the time when the notch occurs in FIG. 7 (i.e., when the aortic valve is closed):

$$SV = \int_{t0}^{t1} SV(t)dt \tag{8}$$
$$= \alpha \int_{t0}^{t1} \frac{dP(t)}{dt}dt + \int_{t0}^{t1} \frac{P(t)}{R}dt$$
$$= \alpha[P(t1) - P(0)] + \frac{1}{R}\int_{t0}^{t1} P(t)dt$$

On the other hand, after the aortic valve has been closed (i.e., after the notch has occurred), SV(t)=0. Thus, Equation (1) may be rewritten into the following Equation (9):

$$\frac{dV(t)}{dt} = -Q(t) \tag{9}$$

Supposing the amount Q(t) of blood flowing out into the capillaries is proportional to the blood pressure P(t) and inversely proportional to the total peripheral vascular resistance R, the following Equation (10) is satisfied:

$$Q(t) = \frac{P(t)}{R} \tag{10}$$

The following Equation (11) is derived by substituting Equation (10) for Equation (9):

$$\frac{dV(t)}{dt} = -\frac{P(t)}{R} \tag{11}$$

Furthermore, even after the aortic valve has been closed, the amount V(t) of the arterial blood flow would be proportional to the blood pressure P(t). That is to say, Equation (5) is satisfied even after the aortic valve has been closed. Thus, the following Equation (12) is derived by substituting Equation (5) for Equation (11):

$$\alpha \frac{dP(t)}{dt} = -\frac{P(t)}{R} \tag{12}$$

The following Equation (13) is derived by performing integration on both sides of Equation (12) in the range of t1-t2:

$$\alpha[P(t2) - P(t1)] = -\frac{1}{R}\int_{t1}^{t2} P(t)dt \tag{13}$$

Equation (13) may be further rewritten into the following Equation (14):

$$R = \frac{-\int_{t1}^{t2} P(t)dt}{\alpha[P(t2) - P(t1)]} \tag{14}$$

The following Equation (15) is derived by substituting Equation (14) for Equation (8):

$$SV = \alpha \left\{ [P(t1) - P(t0)] - [P(t2) - P(t1)]\frac{\int_{t0}^{t1} P(t)dt}{\int_{t1}^{t2} P(t)dt} \right\} \tag{15}$$

On the other hand, the stroke volume $SV_0$ before the dialysis may be given, based on Equation (15), by the following Equation (16):

$$SV_0 = \alpha \left\{ [P_0(t1) - P_0(t0)] - [P_0(t2) - P_0(t1)] \frac{\int_{t0}^{t1} P_0(t)dt}{\int_{t1}^{t2} P_0(t)dt} \right\} \quad (16)$$

In this case, the following Equation (17) for calculating $SV/SV_0$ may be derived from Equations (15) and (16):

$$SV/SV_0 = \frac{[P(t1) - P(t0)] - [P(t2) - P(t1)]\frac{\int_{t0}^{t1} P(t)dt}{\int_{t1}^{t2} P(t)dt}}{[P_0(t1) - P_0(t0)] - [P_0(t2) - P_0(t1)]\frac{\int_{t0}^{t1} P_0(t)dt}{\int_{t1}^{t2} P_0(t)dt}} \quad (17)$$

Equation (17) may be rewritten into Equation (18) for obtaining SV at an arbitrarily point in time based on the initial value $SV_0$ of SV.

$$SV = \frac{[P(t1) - P(t0)] - [P(t2) - P(t1)]\frac{\int_{t0}^{t1} P(t)dt}{\int_{t1}^{t2} P(t)dt}}{[P_0(t1) - P_0(t0)] - [P_0(t2) - P_0(t1)]\frac{\int_{t0}^{t1} P_0(t)dt}{\int_{t1}^{t2} P_0(t)dt}} SV_0 \quad (18)$$

Next, it will be described how to give $SV_0$ at the start of the hemodialysis. First, the cardiac output CO (L/min) is calculated by the following Equation (19) using a cardiac index:

$$CO = CI \times BSA \quad (19)$$

where BSA represents the patient's body surface area ($m^2$) and may be calculated by the Fujimoto formula represented by the following Equation (20):

$$BSA = [88.83 \times HT^{0.663} \times BW^{0.444}]/10000 \quad (20)$$

where HT represents the patient's height (cm), BW represents his or her weight (kg), and CI represents a cardiac index. The value of the patient's cardiac index CI may be considered equal to a normal person's cardiac index 4.0 L/min/$m^2$. This is because even if the patient suffers from cardiac failure, he or she keeps a normal cardiac index by increasing the total body water and also increasing the tonicity of his or her sympathetic nervous system. Thus, the patient's cardiac output is calculated by the following Equation (21):

$$CO = 4 \times BSA \quad (21)$$

If the heart rate is designated by HR, the stroke volume $SV_0$ (ml) may be represented by the following Equation (22):

$$SV_0 = 1000 \times CO/HR \quad (22)$$

The following Equation (23) is derived by substituting Equations (19) and (20) for Equation (22):

$$SV_0 = 4000 \times [88.83 \times HT^{0.663} \times BW^{0.444}]/10000/HR \quad (23)$$

In this case, supposing the number of seconds per heart beat is T2 (sec), the heart rate HR may be given by HR=60/T2. If this equation is substituted for Equation (22), then $SV = 1000 \times CO/(60/T2)$ is satisfied. Meanwhile, $SV_0 = 1000 \times CO_0/(60/T2_0)$ is satisfied. The following Equation (24) is derived by substituting this equation for Equation (18):

$$CO/(60/T2) = \frac{[P(t1) - P(t0)] - [P(t2) - P(t1)]\frac{\int_{t0}^{t1} P(t)dt}{\int_{t1}^{t2} P(t)dt}}{[P_0(t1) - P_0(t0)] - [P_0(t2) - P_0(t1)]\frac{\int_{t0}^{t1} P_0(t)dt}{\int_{t1}^{t2} P_0(t)dt}} \times CO_0/(60/T2_0) \quad (24)$$

Rewriting Equation (24) allows for deriving the following Equation (25) for calculating the cardiac output at an arbitrarily point in time.

$$CO = \frac{[P(t1) - P(t0)] - [P(t2) - P(t1)]\frac{\int_{t0}^{t1} P(t)dt}{\int_{t1}^{t2} P(t)dt}}{[P_0(t1) - P_0(t0)] - [P_0(t2) - P_0(t1)]\frac{\int_{t0}^{t1} P_0(t)dt}{\int_{t1}^{t2} P_0(t)dt}} \times CO_0 \times \frac{T2_0}{T2} \quad (25)$$

Also, the peripheral vascular resistance SVR (mmHg/L/min) at an arbitrarily point in time during the dialysis may be calculated by the following Equation (26) based on the mean blood pressure MBP and the cardiac output CO:

$$SVR = \frac{MBP}{CO} \quad (26)$$

The mean blood pressure MBP may be obtained by the following Equation (27):

$$MBP = \frac{\int_{t0}^{t1} P(t)dt + \int_{t1}^{t2} P(t)dt}{T2} \quad (27)$$

In FIG. 1, illustrated is an example in which the shunt blood vessel is formed in the patient's forearm to measure his or her blood pressure on the forearm. If the shunt blood vessel is formed in his or her upper arm or lower limb, the blood pressure may also be measured in the same way at each of those sites.

Note that the stroke volume at the beginning of a hemodialysis for obtaining a cardiac output is calculated based on a standard value of the cardiac index. Alternatively, an individual patient's value measured by chest ultrasonography may also be used as the stroke volume at the beginning of the hemodialysis.

INDUSTRIAL APPLICABILITY

A blood pressure measuring device according to the present disclosure is able to measure the blood pressure continuously and accurately, and is useful for measuring the blood pressure during a medical treatment or therapy.

DESCRIPTION OF REFERENCE CHARACTERS

110 Strain Sensor
111 Strain Sensor's Body

112 Case
113 Opening
114 Upper portion
115 Lower Portion
120 Band
121 Body Portion
122 Broader portion
123 Holder
130 Control Circuit
132 Driver
133 Processor
150 Pressure Measuring Tool
151 Plastic Cover
152 Gelled Liquid Bag
201 Shunt Blood Vessel

The invention claimed is:

1. A blood pressure measuring device comprising:
a pressure measuring tool;
a fastening member configured to fasten the pressure measuring tool in rest position onto a skin region covering an anastomotic region of a shunt blood vessel without fastening a wrist of a patient: and
a control circuit configured to receive an input signal from the pressure measuring tool and to process the input signal to calculate a pressure inside the anastomotic region of the shunt blood vessel, wherein
the pressure measuring tool includes a strain sensor,
the strain sensor detects an arterial pressure waveform in the anastomotic region, and
the fastening member has an inflexible band configured to wrap around an arm at a site where there is the anastomotic region of the shunt blood vessel.

2. The blood pressure measuring device of claim 1, wherein
the fastening member is configured to keep a distance constant between the pressure measuring tool and a surface of the skin region opposite from the pressure measuring tool.

3. The blood pressure measuring device of claim 1, wherein
a portion of the inflexible band configured to contact with the surface of the skin region opposite from the pressure measuring tool has a larger area than another portion of the inflexible band configured to contact with the pressure measuring tool.

4. The blood pressure measuring device of claim 1, wherein
the pressure measuring tool has a flat plate shape.

5. The blood pressure measuring device of claim 1, wherein
the pressure measuring tool has a curved surface.

6. The blood pressure measuring device of claim 1, wherein
the control circuit continuously processes the input signal received from the pressure measuring tool to calculate a periodic change in pressure inside the anastomotic region as a continuous waveform.

7. The blood pressure measuring device of claim 6, wherein
the control circuit respectively calculates a highest pressure and a lowest pressure inside the anastomotic region based on a local maximum value and a local minimum value of the continuous waveform.

8. The blood pressure measuring device of claim 6, wherein
the control circuit calculates a cardiac output based on the continuous waveform.

* * * * *